United States Patent
Gou et al.

(10) Patent No.: US 11,602,647 B2
(45) Date of Patent: Mar. 14, 2023

(54) METHOD AND APPARATUS FOR DETECTING POSITION, AND RADIOTHERAPY SYSTEM

(71) Applicant: Shenzhen OUR New Medical Technologies Development Co., Ltd., Shenzhen (CN)

(72) Inventors: Tianchang Gou, Xi'an (CN); Jinsheng Li, Shenzhen (CN); Hao Yan, Xi'an (CN); Liang Wang, Shenzhen (CN); Kaiqiang Fu, Xi'an (CN); Pengfei Zhang, Shenzhen (CN); Xiaojun Yue, Shenzhen (CN); Bing He, Shenzhen (CN)

(73) Assignee: SHENZHEN OUR NEW MEDICAL TECHNOLOGIES DEVELOPMENT CO, LTD., Shenzen (CN)

( * ) Notice: Subject to any disclaimer, the term of this patent is extended or adjusted under 35 U.S.C. 154(b) by 72 days.

(21) Appl. No.: 16/931,125

(22) Filed: Jul. 16, 2020

(65) Prior Publication Data
US 2020/0368555 A1   Nov. 26, 2020

Related U.S. Application Data

(63) Continuation of application No. PCT/CN2019/071444, filed on Jan. 11, 2019.

(30) Foreign Application Priority Data

Jan. 19, 2018   (CN) .......................... 201810054586.8

(51) Int. Cl.
*A61N 5/10* (2006.01)
(52) U.S. Cl.
CPC ........... *A61N 5/107* (2013.01); *A61N 5/1048* (2013.01); *A61N 5/1049* (2013.01);
(Continued)

(58) Field of Classification Search
CPC ...... A61N 5/10; A61N 5/1048; A61N 5/1049; A61N 2005/105; A61N 2005/1051;
(Continued)

(56) References Cited

U.S. PATENT DOCUMENTS 6,279,579 B1 * 8/2001 Riaziat ................. A61N 5/1049
128/897
6,690,965 B1 * 2/2004 Riaziat ................... A61B 6/463
600/428

(Continued)

FOREIGN PATENT DOCUMENTS

| CN | 105324155 | 2/2016 |
| CN | 105792746 | 7/2016 |

(Continued)

*Primary Examiner* — Allen C. Ho
(74) *Attorney, Agent, or Firm* — Emerson Thomson Bennett; Roger D. Emerson, Esq.

(57) ABSTRACT

A method and apparatus for position detection, and a radiotherapy system are provided. The radiotherapy system includes: a treatment couch, a positioning apparatus, an optical tracking system and a computer; the positioning apparatus disposed on the treatment couch, and at least one reference point provided on the positioning apparatus; the optical tracking system disposed above the treatment couch and configured to detect relative positioning between a mark point set on a treated part of a patient and the reference point, determine deviation between the relative and reference positions, and send the deviation to the computer. The computer is configured to determine whether to adjust a position of the treatment couch based on the deviation and deviation range. The system provided by the present disclosure avoids the influence of patient movement on the accuracy of treatment, and prevents a treatment beam from damaging normal tissues of the patient.

18 Claims, 9 Drawing Sheets

(52) U.S. Cl.
CPC ......... *A61N 5/1067* (2013.01); *A61N 5/1069* (2013.01); *A61N 5/1084* (2013.01); *A61N 2005/105* (2013.01); *A61N 2005/1051* (2013.01); *A61N 2005/1056* (2013.01); *A61N 2005/1059* (2013.01); *A61N 2005/1061* (2013.01)

(58) Field of Classification Search
CPC .... A61N 2005/1056; A61N 2005/1059; A61N 2005/1061; A61N 5/1064; A61N 5/1065; A61N 5/1067; A61N 5/1069; A61N 5/107; A61N 5/1077; A61N 5/1078; A61N 5/1084
USPC .......................................................... 378/65
See application file for complete search history.

(56) References Cited

U.S. PATENT DOCUMENTS

| | | | | |
|---|---|---|---|---|
| 7,640,607 | B2* | 1/2010 | Guertin | A61B 6/107 5/601 |
| 7,711,087 | B2* | 5/2010 | Mostafavi | A61N 5/1049 378/65 |
| 7,713,205 | B2* | 5/2010 | Fu | A61B 8/08 600/443 |
| 7,729,472 | B2* | 6/2010 | Scherch | A61B 6/0492 378/65 |
| 7,769,430 | B2* | 8/2010 | Mostafavi | A61B 6/541 600/428 |
| 7,853,308 | B2* | 12/2010 | Sauer | A61N 5/1049 378/65 |
| 8,042,209 | B2* | 10/2011 | D'Souza | A61N 5/1049 5/610 |
| 8,090,074 | B2* | 1/2012 | Filiberti | G16H 20/40 378/65 |
| 8,130,907 | B2* | 3/2012 | Maurer, Jr. | A61B 6/00 378/65 |
| 8,189,738 | B2* | 5/2012 | Dussault | A61N 5/103 378/65 |
| 8,417,315 | B2* | 4/2013 | Mostafavi | A61N 5/1049 600/407 |
| 8,417,318 | B2* | 4/2013 | West | A61B 90/36 600/424 |
| 8,536,547 | B2* | 9/2013 | Maurer, Jr. | A61B 6/4447 250/492.1 |
| 8,559,596 | B2* | 10/2013 | Thomson | A61B 6/4071 378/65 |
| 8,784,290 | B2* | 7/2014 | Sumanaweera | A61N 5/1077 600/1 |
| 8,824,630 | B2* | 9/2014 | Maurer, Jr. | A61N 5/1067 378/65 |
| 8,849,633 | B2* | 9/2014 | Core | A61B 6/5264 703/6 |
| 8,900,113 | B2* | 12/2014 | Raleigh | A61N 5/1037 600/1 |
| 8,917,813 | B2* | 12/2014 | Maurer, Jr. | A61B 6/06 378/65 |
| 8,939,920 | B2* | 1/2015 | Maad | A61B 6/541 600/595 |
| 8,989,846 | B2* | 3/2015 | Kuduvalli | A61B 6/4476 600/407 |
| 9,149,654 | B2* | 10/2015 | Handa | A61N 5/1049 |
| 9,153,034 | B2* | 10/2015 | Mostafavi | A61B 6/52 |
| 9,393,444 | B2* | 7/2016 | Suzuki | A61N 5/1031 |
| 9,451,928 | B2* | 9/2016 | Falco | A61B 8/483 |
| 9,486,648 | B2* | 11/2016 | Carey | A61B 90/39 |
| 9,489,734 | B2* | 11/2016 | Gum | A61N 5/1049 |
| 9,508,145 | B2* | 11/2016 | Gum | A61B 6/547 |
| 9,511,243 | B2* | 12/2016 | Yan | G01S 17/66 |
| 9,616,251 | B2* | 4/2017 | Filiberti | A61N 5/107 |
| 9,687,200 | B2* | 6/2017 | Maurer, Jr. | A61B 6/032 |
| 9,717,461 | B2* | 8/2017 | Yu | A61B 5/721 |
| 9,734,589 | B2* | 8/2017 | Yu | A61B 34/20 |
| 9,844,685 | B2* | 12/2017 | Suzuki | A61N 5/1049 |
| 9,883,818 | B2* | 2/2018 | Weber | A61B 5/06 |
| 9,939,130 | B2* | 4/2018 | Jeung | A61B 5/1127 |
| 9,990,711 | B2* | 6/2018 | Lugosi | A61B 6/463 |
| 10,065,049 | B2* | 9/2018 | Lugosi | A61B 6/5288 |
| 10,183,177 | B2* | 1/2019 | Meir | A61N 5/1049 |
| 10,201,717 | B2* | 2/2019 | Berlinger | G06T 7/33 |
| 10,220,181 | B2* | 3/2019 | Giap | A61B 6/037 |
| 10,272,266 | B2* | 4/2019 | Froehlich | A61B 6/486 |
| 10,342,558 | B2* | 7/2019 | Steckner | A61B 17/2256 |
| 10,342,996 | B2* | 7/2019 | Jordan | A61N 5/1083 |
| 10,398,913 | B2* | 9/2019 | Takahashi | A61N 5/1069 |
| 10,426,554 | B2* | 10/2019 | Siewerdsen | A61B 34/20 |
| 10,478,641 | B2* | 11/2019 | Kaneko | A61N 5/10 |
| 10,500,418 | B2* | 12/2019 | Filiberti | A61B 5/113 |
| 10,532,224 | B2* | 1/2020 | Jordan | A61B 5/055 |
| 10,660,583 | B2* | 5/2020 | Haider | A61B 6/0407 |
| 10,702,715 | B2* | 7/2020 | Pearce | A61N 5/1049 |
| 10,750,980 | B2* | 8/2020 | Kaiser | A61B 5/015 |
| 10,751,553 | B2* | 8/2020 | Ueno | A61N 5/1071 |
| 10,828,512 | B2* | 11/2020 | Meir | G16H 50/50 |
| 10,857,391 | B2* | 12/2020 | Stahl | A61B 6/0492 |
| 10,888,483 | B2* | 1/2021 | Ostyn | A61G 13/02 |
| 11,266,857 | B2* | 3/2022 | Berlinger | A61N 5/1068 |
| 11,443,441 | B2* | 9/2022 | Berlinger | A61B 5/0077 |
| 11,478,662 | B2* | 10/2022 | Sayeh | G16H 20/40 |
| 2002/0023652 | A1 | 2/2002 | Riaziat et al. | |

FOREIGN PATENT DOCUMENTS

| | | |
|---|---|---|
| CN | 106139414 | 11/2016 |
| CN | 106943678 | 7/2017 |
| CN | 108273199 | 7/2018 |

* cited by examiner

METHOD AND APPARATUS FOR DETECTING POSITION, AND RADIOTHERAPY SYSTEM

CROSS-REFERENCE TO RELATED APPLICATIONS

This application is a continuation of International Application No. PCT/CN2019/071444 filed on Jan. 11, 2019 and entitled "POSITION DETECTION METHOD AND DEVICE, AND RADIOTHERAPY SYSTEM". The International Application claims priority to Chinese Patent Application No. 201810054586.8, filed on Jan. 19, 2018 and entitled "POSITION DETECTION METHOD AND DEVICE, AND RADIOTHERAPY SYSTEM". The entire disclosures of the prior applications are hereby incorporated by reference in their entirety.

TECHNICAL FIELD

The present disclosure relates to the field of radiotherapy, specifically to a method and apparatus for detecting a position and a radiotherapy system.

BACKGROUND

Radiotherapy equipment generally includes a treatment gantry and a treatment couch. A radiation source is installed on the treatment gantry and can emit a treatment beam. Before radiotherapy, the treatment couch needs to be moved to position a patient to align the target of the patient's treatment body part with the beam focus of the radiation source.

During the radiotherapy, the patient's treatment body part needs to be fixed on the treatment couch by a fixing apparatus. For example, the patient may be fixed on the treatment couch by a fixing apparatus such as a positioning head frame or mask to prevent the patient from moving during the treatment. Therefore, a deviation between the beam focus and the target of the treatment body part may be avoided, the accuracy of the radiotherapy may be ensured, and normal tissues of the patient may also be prevented from being irradiated by the radiation source.

However, when the tightness of the fixing apparatus is low, the patient may have unexpected small actions or movements during the radiotherapy, which may affect the accuracy of the radiotherapy and damage the normal tissues of the patient.

SUMMARY

The present disclosure provides a method and apparatus for detecting a position, and a radiotherapy system. The technical solution is as follows:

In one aspect, a radiotherapy system is provided. The system includes: a treatment couch, a positioning apparatus, an optical tracking system, and a computer;

the positioning apparatus is disposed on the treatment couch, and at least one mark reference point is provided on the positioning apparatus;

the optical tracking system is disposed above the treatment couch, and is configured to detect a relative position between a mark point set on a treatment body part of a patient and the mark reference point, and determine a deviation between the relative position and a reference position, and send the deviation to the computer;

the computer is respectively connected to the optical tracking system and the treatment couch, and is configured to determine whether to adjust a position of the treatment couch based on the deviation and a deviation range.

Alternatively, the optical tracking system includes: an optical detection module, and a detection range of the optical detection module covers an area where the at least one mark reference point is located, and an area where the mark point is located; and the optical detection module is configured to detect a position of each of the mark reference point and a position of the mark point set on the treatment body part of the patient.

Alternatively, the optical detection module includes at least one infrared detector, and each of the infrared detector includes an infrared emitter and a binocular camera; and an infrared reflective material is coated on each of the mark reference point.

Alternatively, the optical detection module further includes:

an image guided radiotherapy (IGRT) system connected to the computer, the IGRT system including at least one set of image acquisition components.

Alternatively, the radiotherapy system further includes: a treatment gantry, on which a plurality of radiation sources are provided; and the optical detection module is disposed above the treatment couch and opposite to the treatment gantry.

Alternatively, the positioning apparatus includes a support frame and a fixing frame, the fixing frame is fixed on the treatment couch, the support frame is rotatably connected with the fixing frame, and the support frame is configured to support the patient, and to adjust a gamma angle of the patient, where the gamma angle is an angle between a plane where a support panel of the support frame is located and a vertical plane, and the vertical plane is perpendicular to a length direction of the treatment couch.

Alternatively, the system further includes: an anti-collision detection apparatus; and the anti-collision detection apparatus is movably connected to the treatment couch, and is configured to move around the treatment couch according to a target trajectory, and detect whether collision with the patient or the positioning apparatus occurs during the movement.

In another aspect, a method for detecting a position is provided, applied to an optical tracking system. The method includes:

detecting a relative position between a mark point set on a treatment body part of a patient and a mark reference point;

determining a deviation between the relative position and a reference position; and sending the deviation to a computer, the computer being configured to determine whether to adjust a position of a treatment couch based on the deviation and a deviation range.

Alternatively, before radiotherapy, the method further includes:

Acquiring, when a positioning of the patient is completed, the relative position between the mark point and the mark reference point, and determining the acquired relative position as the reference position.

Alternatively, the acquiring, when a positioning of the patient is completed, the relative position between the mark point and the mark reference point, and determining the acquired relative position as the reference position, includes:

Acquiring, when the positioning of the patient is completed at an $n^{th}$ gamma angle, the relative position between the mark point and the mark reference point, and determining the acquired relative position as the reference position;

where the $n^{th}$ gamma angle is a gamma angle adjusted by the computer according to a treatment plan instruction before the patient is positioned, the treatment plan includes N gamma angles at which a treatment is to be performed, the N is an integer greater than or equal to 1, the n is sequentially set to an integer from 1 to N, the gamma angle is an angle between a plane where a support panel of a support frame for supporting the patient is located and a vertical plane, and the vertical plane is perpendicular to a length direction of the treatment couch.

In another aspect, a method for detecting a position is provided, applied to a computer. The method includes:

receiving a deviation sent by an optical tracking system, the deviation being a deviation between a relative position and a reference position, the relative position being a relative position between a mark point set on a treatment body part of a patient and a mark reference point detected by the optical tracking system; and determining whether to adjust a position of a treatment couch based on the deviation and a deviation range.

Alternatively, the determining whether to adjust a position of a treatment couch based on the deviation and a deviation range includes one of mode (a), mode (b), or mode (c), where:

the mode (a) includes:

detecting whether the deviation is within the deviation range, and adjusting, when it is detected that the deviation is not within the deviation range, the position of the treatment couch;

the mode (b) includes: detecting whether each deviation received in a first duration is within the deviation range, and adjusting, when it is detected that a number of deviations not within the deviation range is greater than a number threshold, the position of the treatment couch; and the mode (c) includes:

instructing, when it is detected that the received deviation is not within the deviation range, to turn off a radiation source, detecting whether consecutively received M deviations are all within the deviation range in a second duration after the radiation source is turned off, the M being an integer greater than 1, keeping, when the consecutively received M deviations are not within the deviation range, the radiation source off and adjusting the position of the treatment couch, otherwise, instructing to turn on the radiation source, in the second duration.

Alternatively, a radiotherapy process includes: a first stage from the turning on of the radiation source to the completing of the radiotherapy;

the determining whether to adjust a position of a treatment couch based on the deviation and a deviation range includes:

determining whether to adjust the position of the treatment couch according to the mode (b) or the mode (c) in the first stage.

Alternatively, the radiotherapy process further includes: a second stage prior to the first stage;

the determining whether to adjust a position of a treatment couch based on the deviation and a deviation range includes:

determining whether to adjust the position of the treatment couch according to the mode (a) or the mode (b) in the second stage.

Alternatively, before the receiving a deviation sent by an optical tracking system, the method further includes:

receiving a position offset sent by an image guided radiotherapy IGRT system and/or the optical tracking system; and adjusting the position of the treatment couch based on the position offset to perform a position of the patient.

Alternatively, before the patient is positioned, the method further includes:

starting the optical tracking system and the IGRT system, and loading a treatment plan, the treatment plan including N gamma angles at which a treatment to be performed, and N being an integer greater than or equal to 1; and instructing to adjust the gamma angle to an $n^{th}$ gamma angle, according to the treatment plan, the gamma angle being an angle between a plane where a support panel of a support frame for supporting the patient is located and a vertical plane, the vertical plane being perpendicular to a length direction of the treatment couch, and the n being a positive integer less than or equal to N.

Alternatively, an initial value of the n is 1; when the n is less than the N after the positioning and radiotherapy of the patient is completed at the $n^{th}$ gamma angle, the method further includes:

instructing to adjust the gamma angle to an $n+1^{th}$ gamma angle, and updating the n to n+1, according to the treatment plan.

Alternatively, before the computer instructs to adjust the gamma angle to a first gamma angle according to the treatment plan, the method further includes:

Instructing, after the positioning of the patient is completed at any one of the N gamma angles at which a treatment to be performed, to adjust the gamma angle from a first gamma angle to a $N^{th}$ gamma angle sequentially, and instructing an anti-collision detection apparatus to perform simulated anti-collision detection at each of the gamma angles.

In yet another aspect, an apparatus for detecting a position is provided, which may be applied to an optical tracking system. The apparatus includes:

a detection module, configured to detect a relative position between a mark point set on a treatment body part of a patient and a mark reference point;

a determination module, configured to determine a deviation between the relative position and a reference position; and a sending module, configured to send the deviation to a computer, the computer being configured to determine whether to adjust a position of a treatment couch based on the deviation and a deviation range.

In yet another aspect, an apparatus for detecting a position is provided, which may be applied to a computer. The apparatus includes:

a receiving module, configured to receive a deviation sent by an optical tracking system, the deviation being a deviation between a relative position and a reference position, the relative position being a relative position between a mark point set on a treatment body part of a patient and a mark reference point detected by the optical tracking system; and a processing module, configured to determine whether to adjust a position of a treatment couch based on the deviation and a deviation range.

In yet another aspect, an apparatus for detecting a position is provided. The apparatus includes: a processor and a memory, the memory is configured to store instructions executed by the processor, and the processor is configured to perform the instructions stored in the memory to implement the method for detecting a position provided in the above aspect.

In yet another aspect, a computer readable storage medium is provided, having instructions stored therein, when the computer readable storage medium runs on a computer, the computer is enabled to implement the method for detecting a position provided in the above aspect.

BRIEF DESCRIPTION OF THE DRAWINGS

In order to more clearly explain the technical solution in embodiments of the present disclosure, accompanying drawings required in the description of the embodiments will be briefly introduced below. Obviously, the accompanying drawings in the following description are only some embodiments of the present disclosure. For those skilled in the art, without paying any creative work, other accompanying drawings may also be obtained based on these accompanying drawings.

DETAILED DESCRIPTION

To make the objectives, technical solutions, and advantages of the present disclosure more clear, embodiments of the present disclosure will be further described in detail below in conjunction with the accompanying drawings.

Figure 1:
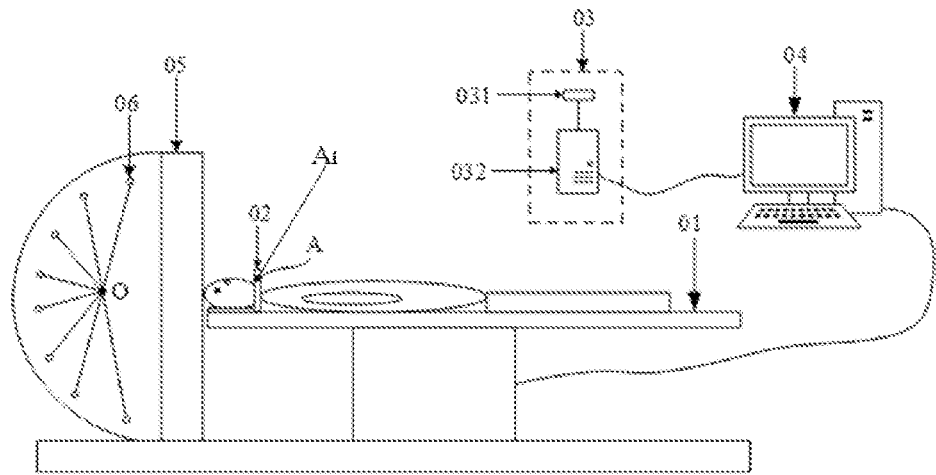
FIG. 1 is a schematic structural diagram of a radiotherapy system provided by an embodiment of the present disclosure.

FIG. 1 is a schematic structural diagram of a radiotherapy system provided by an embodiment of the present disclosure. As shown in FIG. 1, the radiotherapy system may include a treatment couch 01, a positioning apparatus 02, an optical tracking system 03, and a computer 04. The positioning apparatus 02 is disposed on the treatment couch 01, and at least one mark reference point A may be provided on the positioning apparatus 02.

Here, the optical tracking system 03 may be disposed above the treatment couch 01; and the computer 04 is respectively connected to the optical tracking system 03 and the treatment couch 01. During radiotherapy, a patients body surface may be set with a mark point. The optical tracking system 03 may detect the position of the preset mark point on a treatment body part of the patient and the position of each mark reference point A set on the positioning apparatus 02 during the radiotherapy. Therefore, a relative position between the mark point and the mark reference point A, and a deviation between the relative position and a reference position may be determined, and then the optical tracking system 03 may send the deviation to the computer 04. The computer 04 may determine whether to adjust the position of the treatment couch 01 based on the deviation and a deviation range. The deviation range may be pre-stored in the computer 04, and the deviation range may be preset by a treating physician. The computer 04 may be a device having a data processing function, such as a computer or server having a human-computer interaction interface.

In an embodiment of the present disclosure, after the optical tracking system 03 detects the mark point and the position of each mark reference point A, the treating physician may also determine the relative position between the mark point and the mark reference point, and the deviation between the relative position and the reference position, based on the position detected by the optical tracking system 03, and then determine whether the patient moves, that is, determine whether to adjust the position of the treatment couch.

Further, after determining that the patient moves, the treating physician or the computer 04 may adjust the position of the treatment couch in time to reposition the patient. The radiotherapy system has rich functions, and may effectively avoid the influence of patient movement on the accuracy of treatment, and improve the accuracy of radiotherapy.

Alternatively, as shown in FIG. 1, the optical tracking system 03 may include an optical detection module 031, and a detection range of the optical detection module 031 may cover an area where the at least one mark reference point A is located, and an area where the mark point set on the patient's body surface is located. The optical detection module 031 may emit detection light, so as to detect the mark point set on the treatment body part of the patient and the position of each mark reference point.

Alternatively, as shown in FIG. 1, the optical tracking system 03 may further include a processing module 032, and the processing module 032 may be connected to the optical detection module 031 and the computer 04, respectively. For example, the processing module 032 may establish a connection with other devices through a wired network or a wireless network.

In an embodiment of the present disclosure, the optical detection module 031 may send a detected position to the processing module 032. The processing module 032 may calculate the relative position between the mark point and each mark reference point, and calculate the deviation between the relative position and the pre-stored reference position, and then send the deviation to the computer 04, so that the computer 04 may determine whether to adjust the position of the treatment couch based on the deviation and the deviation range, thereby realizing automatic control of the treatment couch and improving the efficiency and accuracy when adjusting the position of the treatment couch.

It can be seen that with reference to FIG. 1 the radiotherapy system may further include a treatment gantry 05, which is provided with a plurality of radiation sources 06, and the treatment beams emitted by the plurality of radiation sources 06 may intersect at one point O, which is the beam focus. During the radiotherapy, it is necessary to ensure that the target of the patient's treatment body part is aligned with the beam focus O. As shown in FIG. 1, the optical detection module 031 may be disposed above the treatment couch 01 and is disposed opposite to the treatment gantry 05.

Alternatively, in an embodiment of the present embodiment, the optical detection module 031 may include at least one infrared detector. The infrared detector may emit infrared rays and be able to receive infrared rays reflected by the mark point and each mark reference point, and then may determine the position of the mark point and each mark reference point based on the received infrared rays.

Correspondingly, each mark reference point A set on the positioning apparatus 02 and the mark point set on the patient's body surface may be coated with an infrared reflective material that can effectively reflect infrared to improve the positioning accuracy of the infrared detector to the mark point and the mark reference point A. Here, the mark point and each mark reference point A may be a spherical structure, and the spherical structure may be formed of a carbon fiber material, and the surface of the carbon fiber material is coated with the infrared reflective material Ai. The infrared reflective material Ai may include at least one of carbon, graphite, oxide, and carbide.

Alternatively, each infrared detector may include an infrared emitter and a binocular camera. The infrared emitter may emit infrared rays, and the binocular camera may detect infrared rays reflected by the mark point and each mark reference point. Each infrared detector may determine the position of the mark point and each mark reference point based on the principle of binocular positioning.

Figure 2:
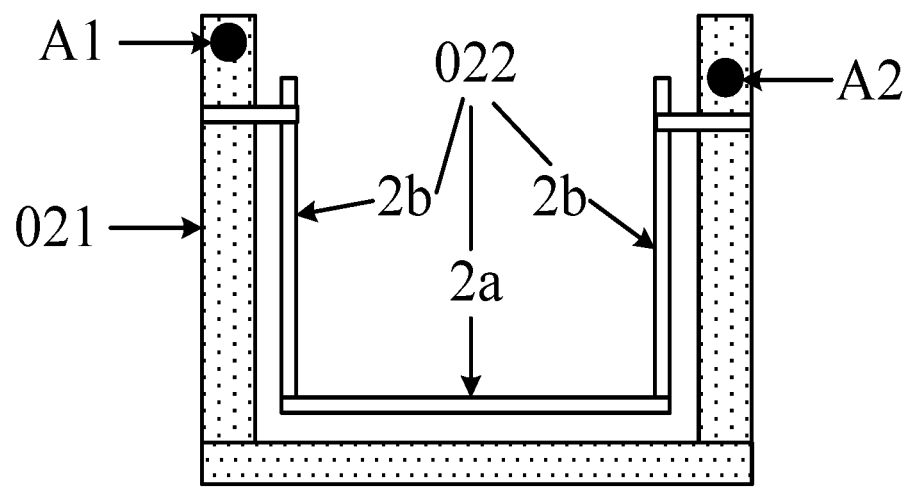
FIG. 2 is a schematic structural diagram of a positioning apparatus provided by an embodiment of the present disclosure.

FIG. 2 is a schematic structural diagram of a positioning apparatus 02 provided by an embodiment of the present disclosure, as shown in FIG. 2, the positioning apparatus 02 may be provided with two mark reference points A1 and A2, and the line between the two mark reference points A1 and A2 may not be parallel to the horizontal plane or the couch surface of the treatment couch 01.

Figure 3:
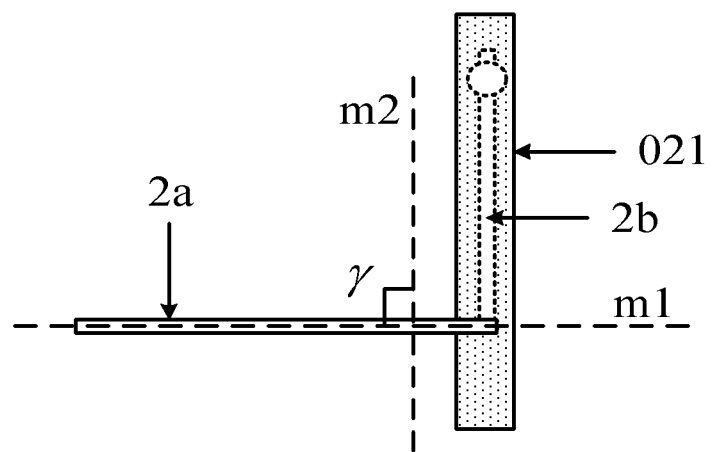
FIG. 3 is a side view of a positioning apparatus provided by an embodiment of the present disclosure.
Figure 4:
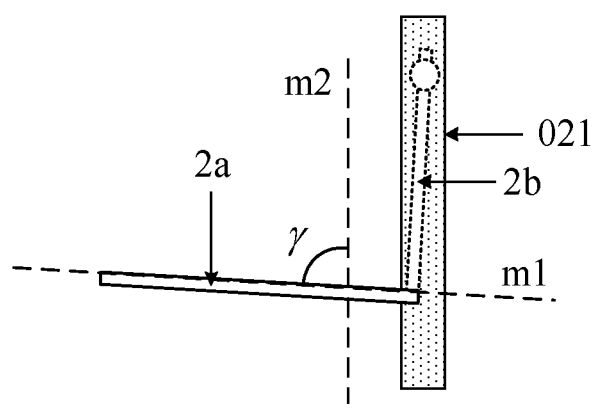
FIG. 4 is a side view of another positioning apparatus provided by an embodiment of the present disclosure.

It can be seen that with reference to FIG. 2 the positioning apparatus 02 may include a fixing frame 021 and a support frame 022, the fixing frame 021 may be fixed on the treatment couch 01, and the support frame 022 is rotatably connected with the fixing frame 021. FIGS. 3 and 4 are side views of the positioning apparatus 02 provided by an embodiment of the present disclosure. It can be seen in conjunction with FIGS. 3 and 4 that the support frame 022 may, include a support panel 2a for supporting the patient's affect part (e.g., the head), and two oppositely disposed connecting rods 2b, one end of each connecting rod 2b is fixedly connected to the support panel 2a, and the other end is rotatably connected to the fixing frame 021, for example, may be connected to the fixing frame 021 through a rotating shaft. Comparing FIGS. 3 and 4, it can be seen that the connecting rod 2b may drive the support panel 2a to rotate in a vertical plane, so that a gamma angle of the patient may be adjusted. As shown in FIGS. 3 and 4, the gamma angle may refer to the angle γ between the plane m1 where the support panel 2a of the support frame is located and the vertical plane m2. The vertical plane m2 may be a plane perpendicular to the horizontal plane and perpendicular to the length direction of the treatment couch 01.

It can also be seen that with reference to FIG. 2 the fixing frame 021 may be a U-shaped frame composed of one support bar and two rails. In addition, a mark reference point may be set on each of the rails.

Alternatively, the radiotherapy system may further include: an anti-collision detection apparatus (not shown in FIGS. 1 to 4). The anti-collision detection apparatus is movably connected to the treatment couch 01, and is configured to move around the treatment couch 01 according to a target trajectory, and detect whether a collision with the patient or the positioning apparatus 02 occurs during the movement. Here, the target trajectory may be a preset fixed trajectory, or the target trajectory may also be adjusted by the treating physician according to actual conditions.

Figure 5:
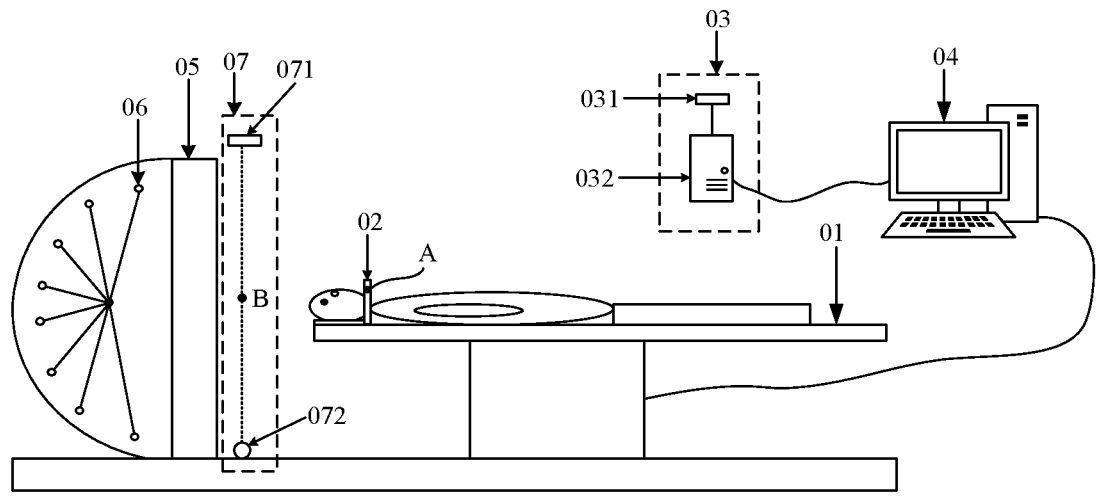
FIG. 5 is a schematic structural diagram of another radiotherapy system provided by an embodiment of the present disclosure.

FIG. 5 is a schematic structural diagram of another radiotherapy system provided by an embodiment of the present disclosure, as shown in FIG. 5, the radiotherapy system may further include an image guide radiation therapy (IGRT) system 07. The IGRT system 07 may include a plurality of sets of image acquisition components, and each set of image acquisition components may include a detector 071 and a bulb 072 that are oppositely disposed. The bulb 072 may emit rays (for example, X-rays), the detector may be a flat panel detector, the detector may receive the rays emitted by the bulb, and the IGRT system 07 may generate IGRT images based on the rays received by the detectors 071. The rays emitted by the bulbs 072 in the plurality of groups of image acquisition components in the IGRT system may intersect at a point B, which is the imaging point of the IGRT system.

Figure 6:
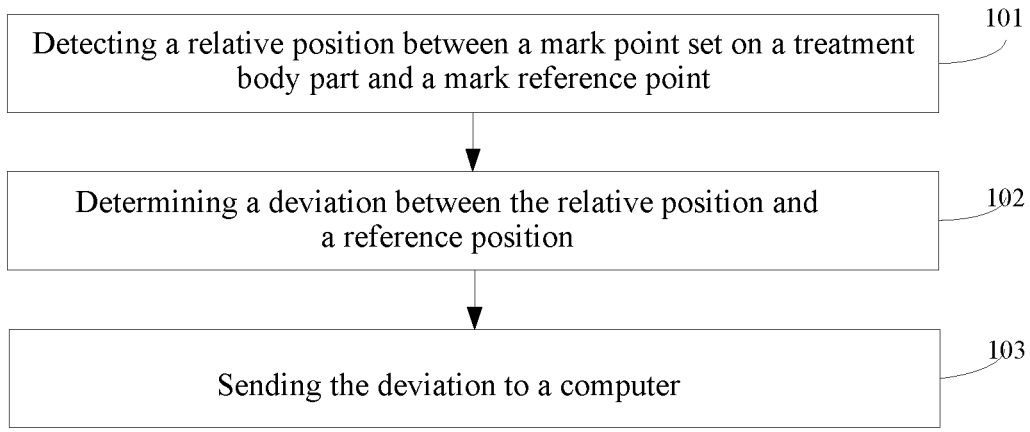
FIG. 6 is a flowchart of a method for detecting a position provided by an embodiment of the present disclosure.

FIG. 6 is a flowchart of a method for detecting a position provided by an embodiment of the present disclosure. The method may be applied to the optical tracking system 03 shown in FIG. 1. Referring to FIG. 6, the method may include:

Step 101, detecting a relative position between a mark point set on a treatment body part of the patient and a mark reference point.

In an embodiment of the present disclosure, as shown in FIG. 1, the positioning apparatus 02 of the treatment couch 01 is provided with at least one mark reference point A, and before the radiotherapy, the patient's affect part may also be preset with a mark point. During the radiotherapy, the optical detection module 031 in the optical tracking system 03 may detect the position of the mark point and the position of each mark reference point in real time, and send the detected position to the processing module 032. The processing module 032 may calculate the relative position between the mark point and each mark reference point. For example, the processing module 032 may determine a reference origin based on the mark point and the at least one mark reference point, and calculate the coordinates of the mark point and each mark reference point relative to the reference origin, which may also be referred to as measured coordinates.

Step 102, determining a deviation between the relative position and a reference position.

The reference position may be the relative position between the mark point and each mark reference point when the radiotherapy system completes a positioning of the patient before the radiotherapy. For example, the reference position may be the coordinates of the mark point and each mark reference point relative to the reference origin when the positioning is completed, and the coordinates may also be referred to as reference coordinates. When determining the deviation, an average value of the Euclidean distance between the mark point and each mark reference point when the positioning ends may first be calculated based on the reference coordinates, and the average value is used as a reference distance; then based on the measured coordinates, an average value of the Euclidean distance between the mark point and each mark reference point during the radiotherapy is calculated, and the average value is a measured distance. Correspondingly, the deviation may refer to the difference between the measured distance and the reference distance.

Step 103, sending the deviation to a computer.

After the optical tracking system sends the calculated deviation to the computer, the computer may determine whether the patient moves based on the deviation and the deviation range, and may adjust the position of the treatment couch in time to reposition the patient after determining that the patient moves, avoiding the deviation between the target of the treatment body part of the patient and the focus of the treatment beam to affect the accuracy of radiotherapy.

In summary, an embodiment of the present disclosure provides a method for detecting a position. The method may detect the relative position between the mark point set on the patient's treatment body part and the mark reference point using the optical tracking system during the radiotherapy, and determine the deviation between the relative position and the reference position, so that the computer may determine whether the patient moves based on the deviation and the deviation range, and may adjust the position of the treatment couch in time to reposition the patient after determining that the patient moves. Therefore, the method provided by the embodiment of the present disclosure may avoid the influence of patient movement on the accuracy of treatment, and may prevent a treatment beam from damaging normal tissues of the patient.

Figure 7:
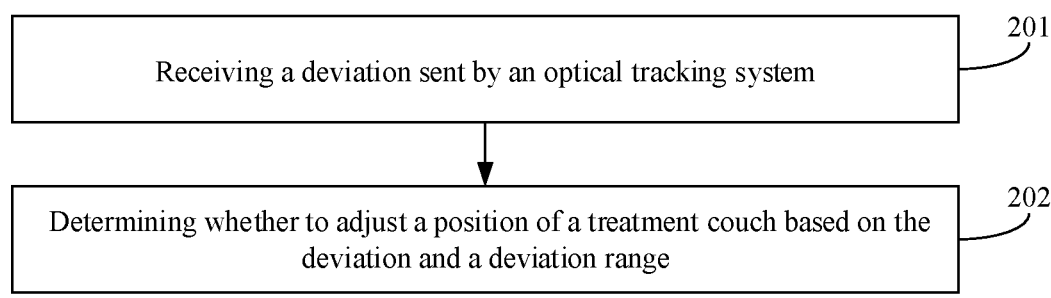
FIG. 7 is a flowchart of another method for detecting a position provided by an embodiment of the present disclosure.

FIG. 7 is a flowchart of another method for detecting a position provided by an embodiment of the present disclosure. The method may be applied to the computer 04 shown in FIG. 1. Referring to FIG. 7, the method may include:

Step 201, receiving a deviation sent by an optical tracking system.

Here, the deviation may be a deviation between a relative position and a reference position, the relative position is a relative position between a mark point preset on a treatment body part of the patient and a mark reference point detected by the optical tracking system during radiotherapy.

In an embodiment of the present disclosure, the optical tracking system may work according to a preset working frequency, that is, the optical tracking system may detect the relative position between the mark point and the mark reference point according to the preset working frequency, calculate and send the deviation. Therefore, during the radiotherapy, the computer may receive at least one deviation sent by the optical tracking system according to the working frequency.

Step 202, determining whether to adjust a position of a treatment couch based on the deviation and a deviation range.

The deviation range is a deviation range predetermined by the treating physician. For example, the deviation range may be 0 to 3 millimeters (mm). In an embodiment of the present disclosure, when the computer detects that the received deviation is not within the deviation range (or, it is detected that the number of deviations not within the deviation range is greater than a number threshold, in the deviations received in a first duration), it may be determined that the patient moves and there is a deviation between the target of the treatment body part of the patient and the focus of the treatment beam, so that the position of the treatment couch needs to be adjusted to reposition the patient. Correspondingly, when the computer detects that the received deviation is within the deviation range (or, in the deviations received in the first duration, it is detected that the number of deviations not within the deviation range is not greater than the number threshold), it may be determined that the patient's posture meets the needs of treatment accuracy without adjusting the position of the treatment couch.

In summary, an embodiment of the present disclosure provides a method for detecting a position. During the radiotherapy, the computer may determine whether the patient moves based on the deviation between the relative position determined by the optical tracking system and the reference position, and may adjust the position of the treatment couch in time to reposition the patient after determining that the patient moves. Therefore, the method provided by the embodiment of the present disclosure may avoid the influence of patient movement on the accuracy of treatment, and may prevent a treatment beam from damaging normal tissues of the patient.

Figure 8:
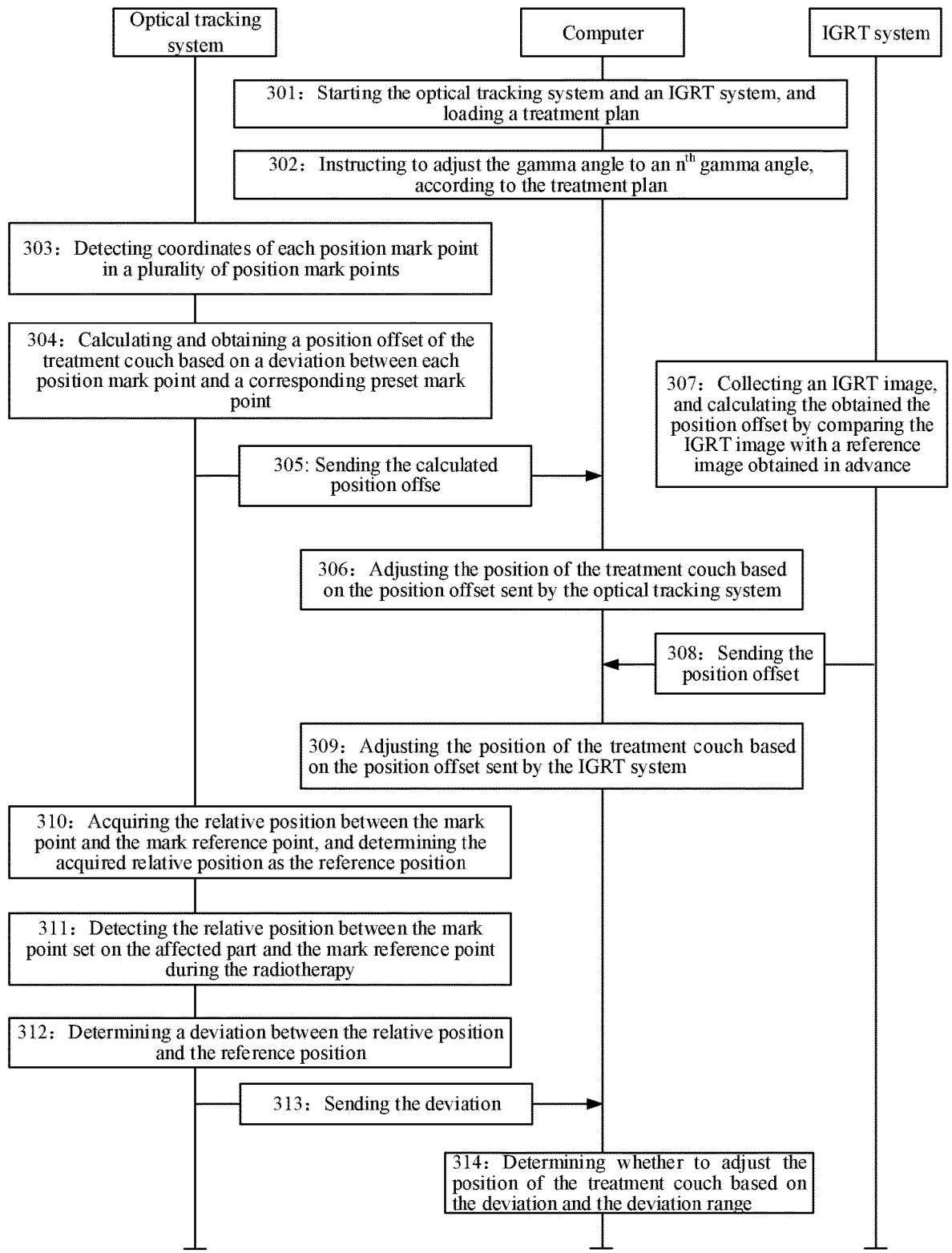
FIG. 8 is a flowchart of yet another method for detecting a position provided by an embodiment of the present disclosure.

FIG. 8 is a flowchart of yet another method for detecting a position provided by an embodiment of the present disclosure. The method may be applied to the radiotherapy system shown in FIG. 5. Referring to FIG. 8, the method may include:

Step 301, a computer starting the optical tracking system and an IGRT system, and loading a treatment plan.

The treatment plan may include N gamma angles treatment is to be performed, and the N is an integer greater than or equal to 1.

Step 302, the computer instructing to adjust the gamma angle to an $n^{th}$ gamma angle, according to the treatment plan.

The initial value of the n may be 1, and n may be a positive integer less than or equal to N. After the adjustment of the gamma angle is completed, the radiotherapy system may perform positioning and radiotherapy on the patient at the current gamma angle (i.e., the nth gamma angle). When n is less than N after the positioning of the patient and radiotherapy is completed at the $n^{th}$ gamma angle, the computer may instruct to adjust the gamma angle to the $n+1^{th}$ gamma angle according to the treatment plan and continue to position and radiotherapy on the patient at the $n+1^{th}$ gamma angle, that is, update n to n+1 and continue to perform this step 302 until the radiotherapy for all N gamma angles is completed. That is, in an embodiment of the present disclosure, the computer may sequentially set n to an integer from 1 to N, and sequentially perform positioning and radiotherapy on the patient at the $n^{th}$ gamma angle.

Figure 9:
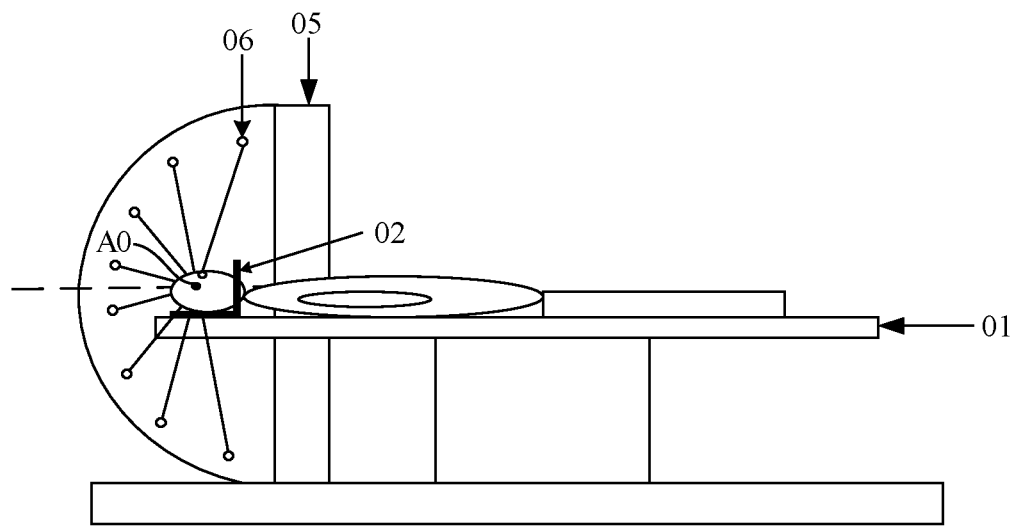
FIG. 9 is a schematic diagram of a patient's posture in a radiotherapy process provided by an embodiment of the present disclosure.
Figure 10:
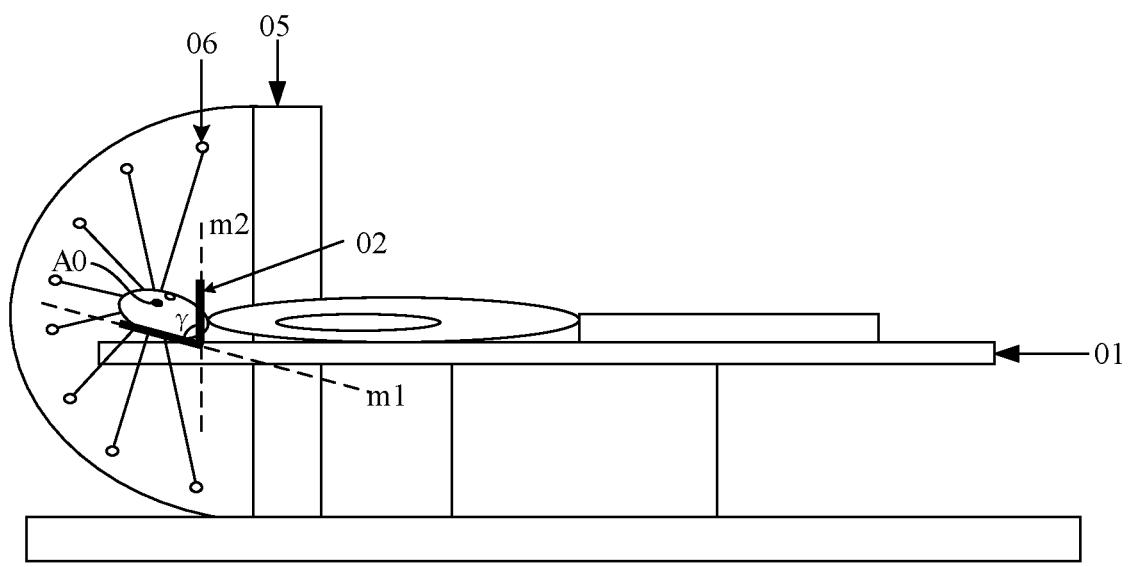
FIG. 10 is a schematic diagram of a patient's posture in another radiotherapy process provided by an embodiment of the present disclosure

For example, assuming that the patient's treatment body part is located on the head. Since a head radiotherapy equipment usually needs to adjust the position angle of the patient's head (that is, the gamma angle), so that the patient's sensitive tissues (such as eyes, brain stem, optic nerve, and optic chiasm) can avoid exposure to a radiation source. As shown in FIG. 9, when the patient is lying on the treatment couch 01 (the gamma angle is 90 degrees), when the treatment beam emitted by the radiation source irradiates a target A0, it may pass through the patient's sensitive tissues or organs, such as eyes. Therefore, as shown in FIG. 10, the treating physician may choose to perform the treatment at a gamma angle of 70 degrees. Referring to FIG. 10, the gamma angle may be an angle γ between a plane m1 where the support panel of the positioning apparatus 02 is located and a vertical plane m2 (i.e., a plane perpendicular to the horizontal plane and perpendicular to the length direction of the treatment couch).

Assuming that the treatment plan includes three (i.e., N=3) gamma angles at which a treatment is to be performed, the three gamma angles at which a treatment is to be performed are 70 degrees, 90 degrees, and 110 degrees, respectively, and the current positioning apparatus fixes the patient's head at a gamma angle of 70 degrees. For the gamma angle of 70 degrees, the computer may first combine the optical tracking system and the IGRT system to position the patient, and then perform radiotherapy on the patient; then perform positioning and radiotherapy on the patient with the gamma angle of 90 degrees, and finally perform positioning and radiotherapy on the patient at the gamma angle of 110 degrees. For the positioning process, reference may be made to the following steps 303 to 309, and for the radiotherapy process, reference may be made to the following steps 310 to 314.

It should be noted that when the gamma angle is introduced in the treatment plan, in order to avoid the patient's treatment body part (such as the head) colliding with the radiotherapy equipment when performing treatment at different gamma angles, before the computer instructs to adjust the gamma angle to the first gamma angle according to the treatment plan, that is, before the above step 302, simulated anti-collision detection needs to be performed on the patient.

For example, the gamma angle may be first adjusted to the $m^{th}$ gamma angle (the m may be any integer from 1 to N), and then the positioning of the patient is completed at the $m^{th}$ gamma angle. Then, the computer may instruct to adjust the gamma angle to the $1^{st}$ to $N^{th}$ gamma angles sequentially, and instruct the anti-collision detection apparatus to perform simulated anti-collision detection at each gamma angle. That is, after completing the positioning of the patient with at gamma angle to the $1^{st}$ to $N^{th}$ gamma angles sequentially, and instruct the anti-collision detection apparatus to perform simulated anti-collision detection at each gamma angle.

During the simulated anti-collision detection, the treating physician may first plug the anti-collision detection apparatus (such as an anti-collision detection rocker) at a designated position, and then the treating physician (or the computer) may control the anti-collision detection apparatus according to a target trajectory to move around the treatment couch to detect whether the anti-collision detection apparatus collides with the patient or the positioning apparatus (such as attachment of a head fixing apparatus). After the anti-collision detection apparatus completes the simulated anti-collision detection, the treating physician may determine whether a result of the simulated anti-collision detection may be accepted based on the number of collisions. In addition, the treating physician may indicate the result of the simulated anti-collision detection to the computer by operation. The result may be detection passes or detection fails. If the computer detects that the result is detection passes, the radiotherapy may be continued. If it is detected that the result of the simulated anti-collision detection is detection fails, the treatment process may be suspended to reposition the patient.

When the treatment plan includes a plurality of gamma angles at which a treatment is to be performed, the computer may control the anti-collision detection apparatus to perform simulated anti-collision detection at each gamma angle, respectively, and may obtain the collision detection result at each gamma angle.

For example, after the treating physician adjusts the gamma angle to 70 degrees, the computer may instruct the anti-collision detection apparatus to start performing simulated anti-collision detection. After the anti-collision detection apparatus completes the simulated anti-collision detection, the computer may obtain the result of the simulated anti-collision detection.

Then, after the treating physician adjusts the gamma angle to 90 degrees, the computer may instruct the anti-collision detection apparatus to start performing simulated anti-collision detection again. After the anti-collision detection apparatus completes the simulated anti-collision detection, the computer may obtain the result of the simulated anti-collision detection again.

Further, after the treating physician adjusts the gamma angle to 110 degrees, the computer may instruct the anti-collision detection apparatus to start performing simulated anti-collision detection. After the anti-collision detection apparatus completes the simulated anti-collision detection, the computer may obtain the result of the simulated anti-collision detection.

After the computer obtains the results of the plurality of collision detection, it may determine whether the treatment plan needs to be re-planed based on the results of the collision detection. If it is determined that the treatment plan does not need to be re-planed, it may continue to perform step 302, that is, start radiotherapy; otherwise, re-plan the treatment plan.

Here, the process of the computer determining whether the treatment plan needs to be re-planed based on the results of the plurality of collision detection may include:

When the results of the plurality of collision detection are all detection passes, it may be determined that there is no need to re-plan the treatment plan.

When the number of failed detection in the results of the plurality of collision detection is greater than or equal to a number threshold, it may be determined that the treatment plan needs to be re-planed. For example, when the number of failed detection in three collision detection results is greater than or equal to 2, it may be determined that the treatment plan needs to be re-planed.

When the number of failed detection in the results of the plurality of collision detection is greater than 0 but less than the number threshold, the computer may display prompt information, and the treating physician may determine whether to continue radiotherapy based on the prompt information. If the treating physician determines that radiotherapy may continue, step 302 may be continued; otherwise, the treatment plan needs to be re-planed.

Step 303, the optical tracking system detecting coordinates of each position mark point in a plurality of position mark points.

In an embodiment of the present disclosure, after the computer instructs to adjust the gamma angle to the $n^{th}$ gamma angle, the optical tracking system may be used to preliminary position the patient before radiotherapy. During the preliminary position, a plurality of position mark points may be set on the patient's body surface, and the optical detection module in the optical tracking system may detect the coordinates of each position mark point in real time. Here, the plurality of position mark points may be used as mark points for detecting the positioning of the patient during the radiotherapy.

Step 304, the optical tracking system calculating and obtaining a position offset of the treatment couch based on a deviation between each position mark point and a corresponding preset mark point.

Before radiotherapy, the patient is computerized tomography (CT) scanned. When obtaining a CT image of the patient, a plurality of preset mark points may be set on the patient's body surface, and the optical tracking system may record the coordinates of each preset mark point in advance.

During the preliminary positioning, the plurality of position mark points set on the patient's body surface correspond to the plurality of preset mark points one-to-one. That is, the set position of each position mark point is the same as the set position of a corresponding preset mark point. Or, the plurality of position mark points may be the plurality of preset mark points. The optical tracking system may calculate the deviation between each position mark point and the corresponding preset mark point based on the pre-recorded coordinates of each preset mark point and the detected coordinates of each position mark point. The deviation may be an offset distance of the position mark point relative to the preset mark point. Further, the optical tracking system may calculate and obtain the position offset of the treatment couch based on the determined deviations of the plurality of position mark points.

For example, since a plurality of preset mark points have been set on the patient's body surface during CT scanning, a relative positional relationship between each preset mark point and the target may be predetermined based on the CT image. During the preliminary positioning, the optical tracking system may infer the coordinates of the target in the optical coordinate system based on coordinates of each position mark point actually acquired in its optical coordinate system (for example, infrared coordinate system). Then, the coordinates of each position mark point and the coordinates of the target are converted into coordinates (also called IEC coordinates) in the three-dimensional coordinate system of the radiotherapy equipment, and the position offset of the treatment couch may be calculated and obtained. The position offset may be three-dimensional data, that is, the position offset may include three sub-data, and each sub-data may be used to indicate an offset of the treatment couch along a coordinate axis in the three-dimensional coordinate system of the radiotherapy equipment.

Step 305, the optical tracking system sending the calculated position offset to the computer.

For example, the processing module of the optical tracking system may send the calculated position offset to the computer. Alternatively, before sending the data, the treating physician may also first determine whether the position offset is within the deviation range. When it is determined that the position offset is within the deviation range, it may be determined that there is no need to adjust the position of the treatment couch, and the treating physician may control the optical tracking system to end the positioning operation. When it is determined that the position offset is not within the deviation range, the treating physician may control the optical tracking system to continue the positioning operation.

Step 306, the computer adjusting the position of the treatment couch based on the position offset sent by the optical tracking system.

After receiving the position offset sent by the optical tracking system, the computer may adjust the position of the treatment couch based on the position offset to realize the preliminary position of the patient.

Alternatively, in an embodiment of the present disclosure, after receiving the position offset, the computer may also determine whether the position offset is within the deviation range. When the position offset is not within the deviation range, the computer may adjust the position of the treatment couch based on the position offset. When the position offset is within the deviation range, the computer may determine that an error of the preliminary position has met the requirements, and there is no need to adjust the position of the treatment couch.

Step 307, the IGRT system collecting an IGRT image, and calculating the obtained the position offset by comparing the IGRT image with a reference image obtained in advance.

After the preliminary position shown in steps 303 to 306, the IGRT system may also be used to accurately position the patient to further improve the accuracy of the positioning. During the accurate positioning, the IGRT system may collect IGRT images of the patient's treatment area (i.e., target or target volume) using the plurality of groups of image acquisition components, and compare the IGRT images with the reference image obtained in advance, calculate to obtain the position offset. The position offset may be an offset between the imaging point of the IGRT system and a preset filming point in the reference image. Alternatively, the reference image may be a CT image obtained by scanning in advance, or a digitally reconstructed radiograph (DRR) image generated based on the CT image.

In an embodiment of the present disclosure, the position offset may be six-dimensional data, that is, the position offset may include three-dimensional translation data and three-dimensional angle data, where the three-dimensional translation data may include three sub-data, and each sub-data may be used to indicate an offset of the treatment couch in a preset three-dimensional coordinate system along a coordinate axis; and the three-dimensional angle data may also include three sub-data, and each sub-data is used to indicate an offset of the treatment couch in the three-dimensional coordinate system in a plane.

Step 308, the IGRT system sending the position offset to the computer.

For example, the IGRT system may send the calculated position offset including 3D translation data and 3D angle data to the computer.

It should be noted that, in an embodiment of the present disclosure, after calculating the position offset, the IGRT system may display the position offset on its operation interface, and then the treating physician may determine whether the position offset is within an offset range, that is, the offset range is determined by the treating physician. If the treating physician determines that the offset is within the offset range, he/she may trigger a posture completion instruction by a touch operation (such as an operation of clicking the confirm button on the operation interface). After the IGRT system detects the positioning completion instruction, it may determine that the positioning operation is completed, and step 308 is no longer required. If the treating physician determines that the position offset is not within the offset range, the IGRT system may be triggered to continue performing the positioning operation by touch operation, that is, the method shown in steps 307 and 308 above is continued.

Step 309, the computer adjusting the position of the treatment couch based on the position offset sent by the IGRT system.

After receiving the position offset, the computer may adjust the position of the treatment couch based on the position offset to achieve accurate positioning of the patient.

Alternatively, in an embodiment of the present disclosure, after receiving the position offset, the computer may first determine whether the position offset is within the offset range. When the position offset is within the offset range, the computer may determine that the positioning of the patient is consistent with the treatment plan and meet the position requirements, therefore, there is no need to adjust the position of the treatment couch. When the position offset is not within the offset range, the computer may determine that the positioning of the patient does not meet the requirements, so that it may continue to adjust the position of the treatment couch to reposition the patient.

Alternatively, after adjusting the position of the treatment couch, the computer may also send a start instruction to the IGRT system, where the start instruction is used to instruct the IGRT system to perform the above steps 307 and 308 again. Then, the computer may continue to perform step 309 until the position offset received by the computer is within the offset range.

It should be noted that, in an embodiment of the present disclosure, in addition to the accurate positioning of the patient using the IGRT system, other positioning systems may also be used to achieve the accurate positioning, for example, a laser light positioning system may be used, the embodiments of the present disclosure do not have any limitation in this regard.

Step 310, the optical tracking system acquiring the relative position between the mark point and the mark reference point, and determining the acquired relative position as the reference position.

After the computer completes the positioning of the patient at the $n^{th}$ gamma angle, the optical tracking system may acquire the relative position between the mark point and the mark reference point, and store the acquired relative position as the reference position. Here, the reference position may include the coordinates of the mark point and the coordinates of each mark reference point. The coordinates may refer to coordinates in the optical coordinate system (for example, infrared coordinate system) where the optical tracking system is located. Alternatively, the optical tracking system may determine a reference origin based on the mark point and the mark reference point (for example, any mark reference point or mark point may be determined as the reference origin. Or the midpoint of the line connecting two mark reference points may be determined as the reference origin), and then convert the optical coordinate system with the reference origin to obtain a transformed coordinate system, and the coordinates may also refer to coordinates in the transformed coordinate system. Alternatively, the reference position may include a vector between the mark point and each mark reference point.

For example, assuming that the coordinates of the mark point detected by the optical detection module in the transformed coordinate system is (0,0,0), a mark reference point is set on the positioning apparatus, and the coordinates of the mark reference point detected by the optical detection module is (3,4,0), assuming that the unit of coordinate values in the coordinate system is centimeters, the processing module may determine the reference position as the coordinates of the two points in the transformed coordinate system.

Step 311, the optical tracking system detecting the relative position between the mark point set on the treatment body part of the patient and the mark reference point during the radiotherapy.

After completing the positioning of the patient at the $n^{th}$ gamma angle, the radiotherapy of the $n^{th}$ gamma angle may be started on the patient. Before radiotherapy, the patient's treatment body part may be pre-set with a mark point. During the radiotherapy, the optical detection module 031 in the optical tracking system 03 may detect the position of the mark point and the position of each mark reference point on the positioning apparatus in real time, and send the detected position to the processing module 032. The processing module 032 may calculate the relative position between the mark point and each mark reference point.

Correspondingly, referring to the above description for the reference position, the relative position between the mark point and any mark reference point may include the coordinates of the mark point and the any mark reference point in the optical coordinate system, or may include the coordinates of the mark point and the any mark reference point in the transformed coordinate system, or alternatively, may include a vector between the mark point and any mark reference point.

Step 312, the optical tracking system determining a deviation between the relative position and the reference position.

In an embodiment of the present disclosure, when calculating the deviation, the optical tracking system may first determine a first Euclidean distance between the mark point and the mark reference point at the completion of the positioning based on the reference position, and use the first Euclidean distance as a reference distance. Then, based on the relative position, a second Euclidean distance between the mark point and the mark reference point during the radiotherapy may be determined. The second Euclidean distance is a measured distance during the radiotherapy. Then, the difference between the second Euclidean distance and the first Euclidean distance may be determined as the deviation.

If only one mark reference point is provided on the positioning apparatus, after detecting the relative position between the mark point and the mark reference point, the optical tracking system may directly calculate the deviation between the relative position and the reference position.

If a plurality of mark reference points are provided on the positioning apparatus, the first Euclidean distance may refer to an average value of the Euclidean distance between the mark point and each mark reference point. During the radiotherapy, the optical tracking system detects the relative position between the mark point and each mark reference point, and after obtaining a plurality of relative positions, the optical tracking system may determine the second Euclidean distance between the mark point and each mark reference point based on each relative position to obtain a plurality of second Euclidean distances, then may calculate the deviation between each second Euclidean distance and the first Euclidean distance separately to obtain a plurality of deviations. Alternatively, after calculating to obtain the plurality of second Euclidean distances, the optical tracking system may first calculate the average value of the plurality of second Euclidean distances, and then calculate a difference between the average value of the plurality of second Euclidean distances and the second Euclidean distance to obtain the deviation.

For example, assuming that during the radiotherapy, the Euclidean distance between the mark point and the mark reference point detected by the processing module is 5.5 cm, since the Euclidean distance between the mark point and the mark reference point is 5 cm when the positioning is completed, the processing module may calculate that the deviation between the relative position and the reference position is 0.5 cm.

Step 313, the optical tracking system sending the deviation to the computer.

If only one mark reference point is provided on the positioning apparatus, the optical tracking system may directly send the calculated deviation to the computer.

If a plurality of mark reference points are provided on the positioning apparatus, the optical tracking system may first calculate the average value of the plurality of deviations, and then send the average value to the computer.

In an embodiment of the present disclosure, in the above step 311, the optical tracking system may detect the relative position between the mark point preset on the treatment body part of the patient and the mark reference point according to a preset working frequency. Correspondingly, in the above step 312, the optical tracking system may calculate the deviation between the relative position and the reference position according to the working frequency. Correspondingly, in step 313, the optical tracking system may send the deviation to the computer according to the working frequency.

For example, assuming that the working frequency is f, it may be determined that a detection period when the optical tracking system detects the relative position is T=1/f (seconds), that is, the optical tracking system may detect the relative position between the mark point and the mark reference point every T seconds, calculate the deviation between the relative position and the reference position, and send the deviation to the computer.

Step 314, the computer determining whether to adjust the position of the treatment couch based on the deviation and the deviation range.

The deviation range may be predetermined by the treating physician, for example, it may be 0 to 3 mm. Since in an embodiment of the present disclosure, the optical tracking system may send the deviation to the computer according to the preset working frequency, so that each time the computer receives a deviation sent by the optical tracking system, it may detect whether the deviation is within the deviation range.

For example, assuming that the deviation range is 0 to 3 mm, and a certain deviation received by the computer is 0.5 cm, that is, 5 mm, the computer may determine that the deviation is not within the deviation range.

In an embodiment of the present disclosure, the process of the computer determining whether to adjust the position of the treatment couch based on the deviation and the deviation range may be implemented by at least the following:

In a first alternative implementation: the computer may directly detect whether the received deviation is within the deviation range. When it is detected that the deviation is not within the deviation range, the computer may determine that the position of the treatment couch needs to be adjusted. Otherwise, when it is detected that the deviation is within the deviation range, the computer may determine that there is no need to adjust the position of the treatment couch.

In a second alternative implementation: the computer may detect whether each deviation received in a first duration is within the deviation range. When it is detected that the number of deviations not within the deviation range is greater than a number threshold, the computer may adjust the position of the treatment couch. Otherwise, when it is detected that the number of deviations not within the deviation range is not greater than the number threshold, the computer may determine that there is no need to adjust the position of the treatment couch.

In an embodiment of the present disclosure, the computer may count the number of deviations not within the deviation range in the deviations received in the first duration during the radiotherapy. When the number is greater than the number threshold, the computer may determine that the patient moves and there is a deviation between the target of the treatment body part of the patient and the focus of the treatment beam. Therefore, the position of the treatment couch needs to be adjusted to reposition the patient. The first duration and the number threshold may both be pre-stored in the computer, and both may be preset by the treating physician. For example, the first duration may be 10 seconds or 20 seconds, and the number threshold may be 3 or 5.

Figure 11:
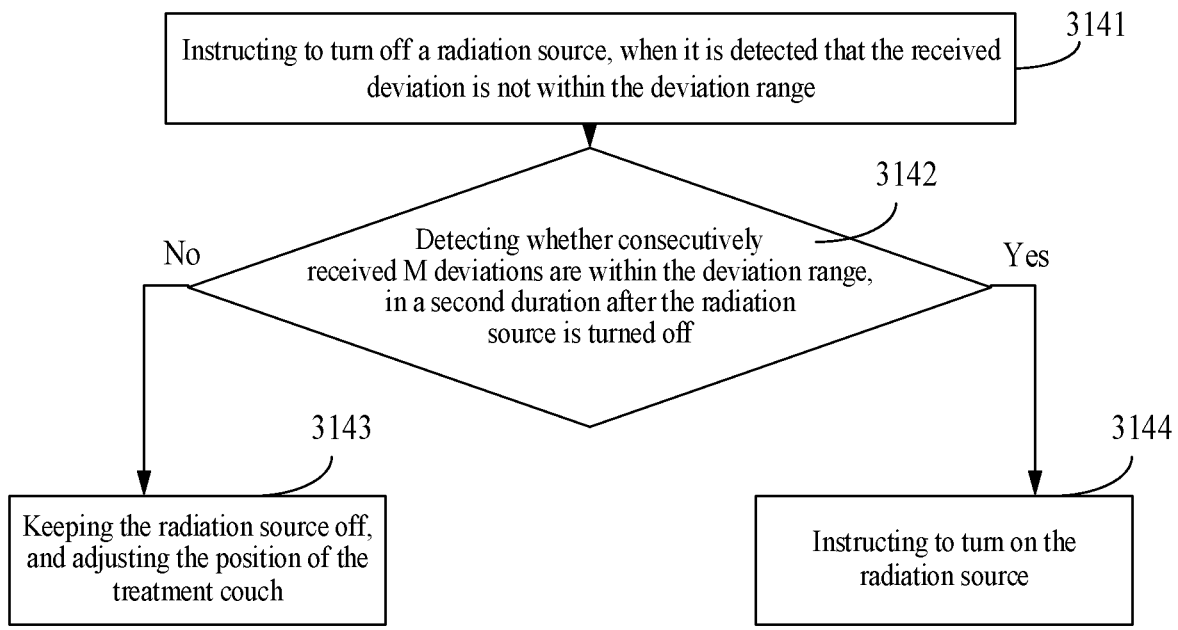
FIG. 11 is a flowchart of a method for adjusting a position of a treatment couch provided by an embodiment of the present disclosure.

In a third alternative implementation: as shown in FIG. 11, the adjustment process may include:

Step 3141, instructing to turn off a radiation source, when it is detected that the received deviation is not within the deviation range.

In an embodiment of the present disclosure, after the radiation source is turned on, when the computer detects that the received deviation is not within the deviation range, for example, when it is detected that the deviation received at a first moment is not within the deviation range, it may be determined that the deviation between a current patient target and the beam focus is large. In order to avoid damage to the patient's normal tissues, the computer may turn off the radiation source in time.

Step 3142: detecting whether consecutively received M deviations are within the deviation range, in a second duration after the radiation source is turned off.

Here, M is an integer greater than 1. In the second duration, when none of the consecutively received M deviations is within the deviation range, the computer may perform step 3143. When the consecutively received M deviations are all within the deviation range, the computer may perform step 3144. The second duration and the value of M may both be pre-stored in the computer, and both may be preset by the treating physician. The second duration and the first duration may be equal or different. For example, the second duration may be 15 seconds or 20 seconds, and M may be 5.

After the computer instructs to turn off the radiation source, in order to further determine whether the deviation is caused by the patient's accidental movement, or the patient's posture actually shifts, the computer may continue to count the number of deviations not within the deviation range in the received deviations in the second duration after the radiation source is turned off. In the second duration, when the computer detects that the consecutively received M deviations are not within the deviation range, or when no consecutive M deviations are detected within the deviation range, it may be determined that the patient's posture actually shifts, so that step 3143 may be performed.

Step 3143, keeping the radiation source off, and adjusting the position of the treatment couch.

In the second duration, when the consecutively received M deviations are not within the deviation range, the computer may determine that the patient's posture actually shifts, so that it may keep the radiation source off and adjust the position of the treatment couch.

For example, assuming that the second duration is 20 seconds and M is 5, when the computer detects that a certain deviation is not within the deviation range, and turns off the radiation source, it may continue to count whether each deviation received is within the deviation range within the next 20 seconds. If the computer detects that 5 consecutive deviations are not within the deviation range within 20 seconds after turning off the radiation source, the radiation source may be kept off and the position of the treatment couch may be adjusted.

Step 3144, instructing to turn on the radiation source.

When the computer detects that the consecutively received M deviations are within the deviation range, it may be determined that the patient's posture returns to normal, so that it may be determined that there is no need to adjust the position of the treatment couch, and may instruct to turn on the radiation source in order to continue the radiotherapy.

For example, when the computer detects that consecutively received 5 deviations are within the deviation range within 20 seconds after turning off the radiation source, it can be determined that the patient returns to a normal position, so that the radiation source may be turned on to continue the radiotherapy.

Figure 12:
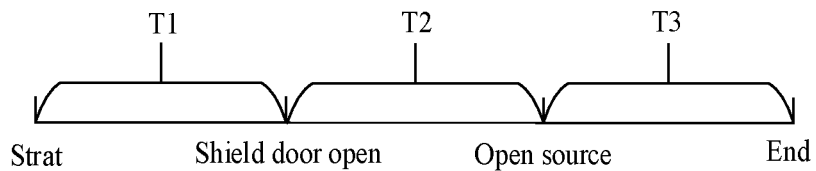
FIG. 12 is a schematic diagram of a stage division of a radiotherapy process provided by an embodiment of the present disclosure.

In an embodiment of the present disclosure, the radiotherapy process on the patient by the radiotherapy system may include: a first stage from the turning on of the radiation source to an end of the radiotherapy, and a second stage before the first stage. Alternatively, as shown in FIG. 12, the second stage may include an initial stage T1 and a preparation stage T2, and the first stage may be a treatment stage T3.

The initial stage T1 in the second stage may be a period from the completion of position to the opening of a radiotherapy equipment shield door; the preparation stage T2 in the second stage may be a period from the opening of the shield door, the entering of the couch to the turning on of the radiation source; and the treatment stage T3 may be a period from the turning on of the radiation source to the end of the radiotherapy.

In an embodiment of the present disclosure, in the initial stage T1, the preparation stage T2 and the treatment stage T3, the optical tracking system may continuously send its calculated deviation to the computer according to the working frequency. For each stage, the computer may adjust the position of the treatment couch in different methods. For example, in the second stage, the computer may adjust the position of the treatment couch using the first or second alternative implementation described above. In the first stage, the computer may adjust the position of the treatment couch using the second or third alternative implementation described above.

Assuming that in the second stage, the computer uses the second alternative implementation to adjust the position of the treatment couch, and the adjustment process may include:

Step S1, in the initial stage T1, detecting whether the number of deviations not within the deviation range is greater than a first threshold N1.

In the initial stage T1, when the number of deviations not within the deviation range is greater than the first threshold N1, the computer may perform step S2; and if in the initial stage T1, the number of deviations not within the deviation range is not greater than the first threshold N1, the computer may determine that the patient's posture meets the requirements of treatment accuracy, so that step S3 may be continued.

Step S2, adjusting the position of the treatment couch.

In the initial stage T1, if the computer counts that the number of deviations not within the deviation range is greater than the first threshold N1, it may be determined that the patient moves, and the patient needs to be repositioned. Therefore, the radiotherapy process may be suspended, and the position of the treatment couch may be readjusted.

Step S3, in the preparation stage T2, detecting whether the number of deviations not within the deviation range is greater than a second threshold N2.

When the computer detects that the number of deviations not within the deviation range is greater than the second threshold N2, step S2 may be performed, that is, the position of the treatment couch is readjusted; and if in the preparation stage T2, the number of deviations not within the deviation range is not greater than the second threshold N2, the computer may determine that the patient's posture meets the requirements of treatment accuracy, so that it may enter the first stage.

Here, N1 and N2 may both be pre-stored in the computer, and both may be preset by the treating physician. Moreover, N1 and N2 may be equal or different, the embodiments of the present disclosure do not have any limitation in this regard.

It should be noted that, in the above step 314, when the computer determines that the position of the treatment couch needs to be adjusted, the method shown in steps 303 to 309 or the method shown in steps 307 to 309 may be used to adjust the position of the treatment couch; or, if the deviation sent by the optical tracking system received by the computer is a three-dimensional deviation, that is, the deviation includes three sub-data, each sub-data is used to indicate an offset of the treatment couch along a coordinate axis in the three-dimensional coordinate system of the radiotherapy equipment, then the computer may also directly adjust the position of the treatment couch based on the three-dimensional deviation. The embodiments of the present disclosure do not limit the method in which the computer adjusts the position of the treatment couch.

It should also be noted that if the treatment plan includes a plurality of gamma angles (for example, three gamma angles), before radiotherapy, the treating physician may adjust the patient's posture to a first gamma angle (for example, 70 degrees), then, the computer may combine the optical tracking system and the IGRT system, refer to the method shown in steps 303 to 309 to position the patient, and then refer to the method shown in steps 310 to 314 to perform radiotherapy on the patient at the first gamma angle.

Further, the treating physician may adjust the gamma angle to a second gamma angle (for example, 90 degrees), then, the computer may combine the optical tracking system and the IGRT system, refer to the method shown in steps 303 to 309 to position the patient again, and then again refer to the method shown in steps 310 to 314 to perform radiotherapy on the patient at the second gamma angle.

Further, the treating physician may adjust the gamma angle to a third gamma angle (for example, 110 degrees), then, the computer may combine the optical tracking system and the IGRT system, refer to the method shown in steps 303 to 309 to position the patient again, and then again refer to the method shown in steps 310 to 314 to perform radiotherapy on the patient at the third gamma angle.

It should be noted that the sequence of the steps of the method for detecting a position provided by the embodiments of the present disclosure may be adjusted appropriately, and the steps may also be increased or decreased according to the situation. For example, steps 303 to 306 may be deleted according to the situation. Those skilled in the art may easily think of a changed method within the technical scope disclosed in the present disclosure, which should be covered within the protection scope of the present disclosure, and thus detailed description thereof will be omitted.

In summary, an embodiment of the present disclosure provides a method for detecting a position. During the radiotherapy, the computer may determine whether the patient moves based on the deviation between the relative position determined by the optical tracking system and the reference position, and may adjust the position of the treatment couch in time to reposition the patient after determining that the patient moves. Therefore, the method provided by the embodiment of the present disclosure may avoid the influence of patient movement on the accuracy of treatment, and may prevent a treatment beam from damaging normal tissues of the patient.

Figure 13:
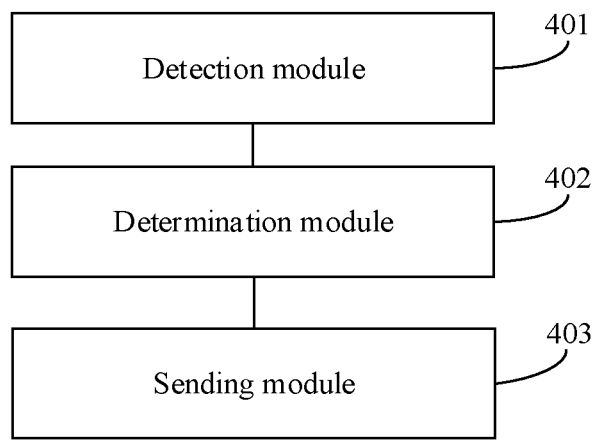
FIG. 13 is a schematic structural diagram of an apparatus for detecting a position provided by an embodiment of the present disclosure.

FIG. 13 is a schematic structural diagram of an apparatus for detecting a position provided by an embodiment of the present disclosure. The apparatus may be applied to the optical tracking system 03 shown in FIG. 1, referring to FIG. 13, the apparatus may include:

a detection module 401, configured to detect a relative position between a mark point set on a treatment body part of an patient and a mark reference point.

a determination module 402, configured to determine a deviation between the relative position and a reference position.

The reference position is the relative position between the mark point and the mark reference point at the end of the position.

a sending module 403, configured to send the deviation to a computer, the computer being configured to determine whether to adjust a position of a treatment couch based on the deviation and a deviation range.

The detection module 401 may be an optical detection module in the optical tracking system 03, and the determination module 402 and the sending module 403 may be integrated in a processing module in the optical tracking system 03.

Figure 14:
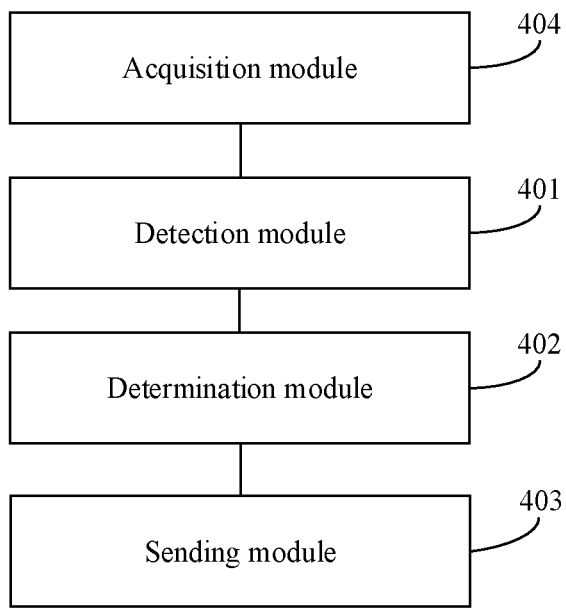
FIG. 14 is a schematic structural diagram of another apparatus for detecting a position provided by an embodiment of the present disclosure.

Alternatively, as shown in FIG. 14, the apparatus may further include:

an acquisition module 404, configured to acquire the relative position between the mark point and the mark reference point, when the positioning of the patient is completed, and determine the acquired relative position as the reference position. The acquisition module 404 may also be integrated in the processing module in the optical tracking system 03.

Alternatively, the detection module 401 may also be configured to detect coordinates of each position mark point in a plurality of position mark points, where the plurality of position mark points are set on the patient's body surface.

The determination module 402 may also be configured to calculate and obtain a position offset of the treatment couch based on a deviation between each position mark point and a corresponding preset mark point, where the plurality of position mark points correspond to the plurality of preset mark points one-to-one.

The sending module 403 may also be configured to send the calculated position offset to the computer, and the computer is configured to adjust the position of the treatment couch based on the position offset.

Alternatively, the acquisition module 404 may be configured to:

acquire a relative position between the mark point and the mark reference point, when positioning of the patient is completed at the $n^{th}$ gamma angle, and determine the acquired relative position as the reference position;

where the $n^{th}$ gamma angle is a gamma angle adjusted by the computer according to a treatment plan instruction before the positioning of the patient is performed, the treatment plan includes N gamma angles at which a treatment is to be performed, the N is an integer greater than or equal to 1, the n is sequentially set to an integer from 1 to N, the gamma angle is an angle between a plane where a support panel of a support frame for supporting the patient is located and a vertical plane, and the vertical plane is perpendicular to a length direction of the treatment couch.

In summary, an embodiment of the present disclosure provides an apparatus for detecting a position. The apparatus may detect the relative position between the mark point set on the patient's treatment body part and the mark reference point during the radiotherapy, and determine the deviation between the relative position and the reference position, so that the computer may determine whether the patient moves based on the deviation, and may adjust the position of the treatment couch in time to reposition the patient after determining that the patient moves. Therefore, the apparatus may avoid the influence of patient movement on the accuracy of treatment, and may prevent a treatment beam from damaging normal tissues of the patient.

Figure 15:
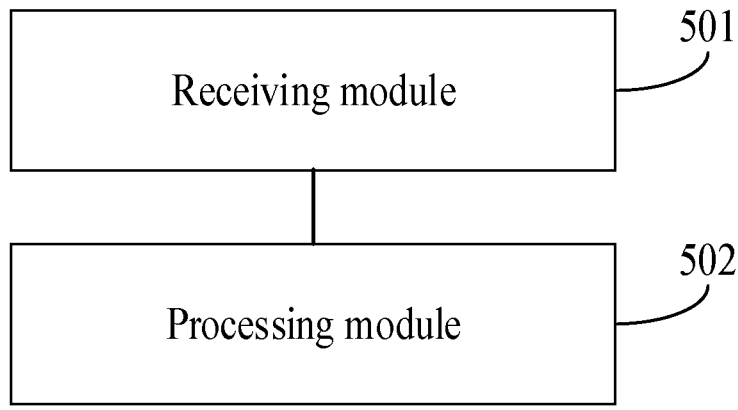
FIG. 15 is a schematic structural diagram of yet another apparatus for detecting a position provided by an embodiment of the present disclosure.

FIG. 15 is a schematic structural diagram of yet another apparatus for detecting a position provided by an embodiment of the present disclosure. The apparatus may be applied to the computer 04 shown in FIG. 1, referring to FIG. 15, the apparatus may include:

a receiving module 501, configured to receive a deviation sent by an optical tracking system, the deviation being a deviation between a relative position and a reference position, the relative position being a relative position between a mark point set on a treatment body part of an patient and a mark reference point detected by the optical tracking system.

a processing module 502, configured to determine whether to adjust a position of a treatment couch based on the deviation and a deviation range.

Figure 16:
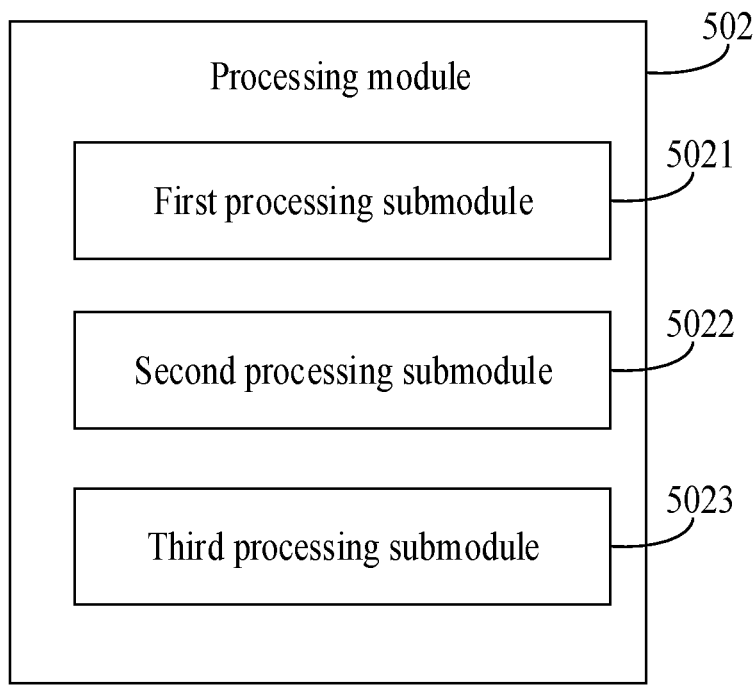
FIG. 16 is a schematic structural diagram of a processing module provided by an embodiment of the present disclosure.

FIG. 16 is a schematic structural diagram of a processing module provided by an embodiment of the present disclosure. As shown in FIG. 16, the processing module 502 may include: a first processing submodule 5021, a second processing submodule 5022, or a third processing submodule 5023.

The first processing submodule 5021, is configured to detect whether the deviation is within the deviation range, and when it is detected that the deviation is not within the deviation range, adjust the position of the treatment couch, otherwise, not adjust the position of the treatment couch.

The second processing submodule 5022, is configured to detect whether each deviation received in a first duration is within the deviation range, and when it is detected that the number of deviations not within the deviation range is greater than a number threshold, adjust the position of the treatment couch, otherwise, not adjust the position of the treatment couch.

The third processing submodule 5023, is configured to instruct to turn off a radiation source, when it is detected that the received deviation is not within the deviation range; detect whether consecutively received M deviations are all within the deviation range in a second duration after the radiation source is turned off, the M being an integer greater than 1; and in the second duration when the consecutively received M deviations are not within the deviation range, keep the radiation source off and adjust the position of the treatment couch, otherwise, instruct to turn on the radiation source, and not adjust the position of the treatment couch.

Alternatively, a radiotherapy process may include: a first stage from the turning on of the radiation source to an end of the radiotherapy; in the first stage, the second processing submodule 5022 or the third processing submodule 5023 may be used to determine whether to adjust the position of the treatment couch.

Further, the radiotherapy process may further include: a second stage before the first stage.

In the second stage, the first processing submodule 5021 or the second processing submodule 5022 may be used to determine whether to adjust the position of the treatment couch.

Figure 17:
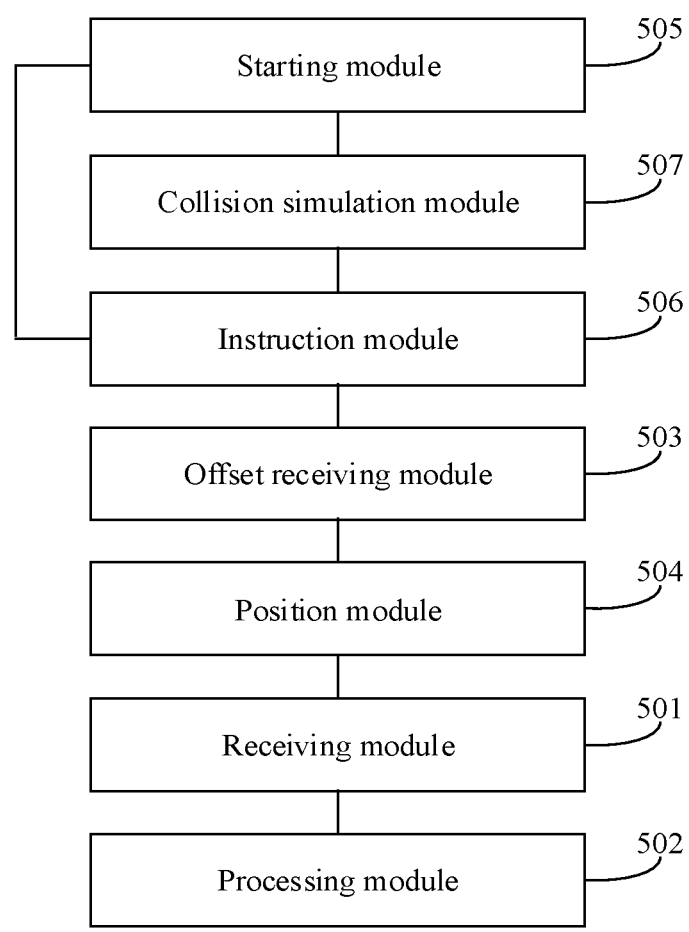
FIG. 17 is a schematic structural diagram of yet another apparatus for detecting a position provided by an embodiment of the present disclosure.

Alternatively, FIG. 17 is a schematic structural diagram of yet another apparatus for detecting a position provided by an embodiment of the present disclosure. Referring to FIG. 17, the apparatus may further include:

an offset receiving module 503, configured to receive a position offset sent by an IGRT system and/or the optical tracking system.

a position module 504, configured to adjust the position of the treatment couch based on the position offset to complete a positioning of the patient.

Alternatively, as shown in FIG. 17, the apparatus may further include:

a starting module 505, configured to start the optical tracking system and the IGRT system, and load a treatment plan, the treatment plan including N gamma angles at which a treatment is to be performed, and N being an integer greater than or equal to 1; and an instruction module 506, configured to instruct to adjust the gamma angle to an $n^{th}$ gamma angle, according to the treatment plan, the gamma angle being an angle between a plane where a support panel of a support frame for supporting the patient is located and a vertical plane, the vertical plane being perpendicular to a length direction of the treatment couch, and the n being a positive integer less than or equal to N.

Alternatively, an initial value of the n is 1; and the instruction module 506 may be further configured to:

when the n is less than the N after the positioning and radiotherapy of the patient is completed at the $n^{th}$ gamma angle, instruct to adjust the gamma angle to an $n+1^{th}$ gamma angle, and update the n to n+1, according to the treatment plan.

Alternatively, as shown in FIG. 17, the apparatus may further include:

A collision simulation module 507, configured to, before the computer instructs to adjust the gamma angle to a first gamma angle according to the treatment plan, instruct to adjust the gamma angle from a first to $N^{th}$ gamma angles sequentially, and instruct an anti-collision detection apparatus to perform simulated anti-collision detection at each of the gamma angles, after completing the positioning of the patient at any one of the N gamma angles at which a treatment is to be performed.

In summary, an embodiment of the present disclosure provides an apparatus for detecting a position. During the radiotherapy, the apparatus may determine whether the patient moves based on the deviation between the relative position determined by the optical tracking system and the reference position, and may adjust the position of the treatment couch in time to reposition the patient after determining that the patient moves. Therefore, the apparatus may avoid the influence of patient movement on the accuracy of treatment, and may prevent a treatment beam from damaging normal tissues of the patient.

Those skilled in the art may clearly understand that for the convenience and conciseness of the description, the working processes of the apparatuses and modules described above may refer to the corresponding processes in the foregoing method embodiments, and detailed description thereof will be omitted.

An embodiment of the present disclosure also provides an apparatus for detecting a position, which may include a processor and a memory, where the memory is configured to store instructions executed by the processor, and the processor is configured to perform the instructions stored in the memory to implement the method for detecting a position provided by the above method embodiments. For example, the method performed by the computer or the method performed by the optical tracking system in the above method embodiments may be implemented.

An embodiment of the present disclosure also provides a computer readable storage medium, having instructions stored therein, when the computer readable storage medium runs on a computer, the computer is enabled to implement the method for detecting a position provided by the above method embodiments. For example, the method performed by the computer or the method performed by the optical tracking system in the above method embodiments may be implemented.

The above are only exemplary embodiments of the present disclosure and are not intended to limit the present disclosure. Any modification, equivalent replacement, improvement, etc. made within the spirit and principle of the present disclosure should be included in the protection scope of the present disclosure.

What is claimed is:

1. A radiotherapy system, comprising:
a treatment couch, a positioning apparatus, an optical tracking system, and a computer,
wherein:
the positioning apparatus including at least one mark reference point is disposed on the treatment couch;
the optical tracking system is disposed above the treatment couch, and is configured to detect a relative position between a mark point set on a treatment body part of a patient and the at least one mark reference point, determine a deviation between the relative position and a reference position, and send the deviation to the computer; and
the computer is respectively connected to the optical tracking system and the treatment couch, and is configured to determine whether to adjust a position of the treatment couch based on the deviation and a deviation range.

2. The radiotherapy system according to claim 1, wherein the optical tracking system comprises: an optical detector disposed above the treatment couch, and a detection range of the optical detector covers an area where the at least one mark reference point is located, and an area where the mark point is located; and
the optical detector is configured to detect a position of each of the at least one mark reference point and a position of the mark point set on the treatment body part of the patient.

3. The radiotherapy system according to claim 2, wherein the optical detector comprises at least one infrared detector, and each of the at least one infrared detector comprises an infrared emitter and a binocular camera; and
each of the at least one mark reference point includes a coating of an infrared reflective material.

4. The radiotherapy system according to claim 1, further comprising:
an image-guided radiotherapy IGRT system connected to the computer, the image-guided radiotherapy IGRT system comprising at least one set of image acquisition components.

5. The radiotherapy system according to claim 1, wherein the positioning apparatus comprises a support frame including a support panel and a fixing frame, the fixing frame is fixed on the treatment couch, the support frame is rotatably connected with the fixing frame, and the support frame is configured to support the patient, and to adjust a gamma angle of the patient, wherein the gamma angle is an angle between a plane, where the support panel is located, and a vertical plane, and the vertical plane is perpendicular to a length direction of the treatment couch.

6. A method for detecting a position, comprising:
detecting a relative position between a mark point set on an treatment body part of a patient and a mark reference point;
determining a deviation between the relative position and a reference position; and
sending the deviation to a computer, the computer being configured to determine whether to adjust a position of a treatment couch based on the deviation and a deviation range.

7. The method according to claim 6, further comprising:
acquiring, when a positioning of the patient is completed, the relative position between the mark point set on the treatment body part of the patient and the mark reference point, and determining the acquired relative position as the reference position.

8. The method according to claim 7, wherein the acquiring, when a positioning of the patient is completed, the relative position between the mark point set on the treatment body part of the patient and the mark reference point, and determining the acquired relative position as the reference position, comprises:
acquiring, when the positioning of the patient is completed at an $n^{th}$ gamma angle, the relative position between the mark point set on the treatment body part of the patient and the mark reference point, and determining the acquired relative position as the reference position;
wherein the $n^{th}$ gamma angle is a gamma angle adjusted by the computer according to a treatment plan before the patient is positioned, the treatment plan comprises N gamma angles at which a treatment is to be performed, N is an integer greater than or equal to 1, n is sequentially set to an integer from 1 to N, the gamma angle is an angle between a plane, where a support panel of a support frame for supporting the patient is located and a vertical plane, and the vertical plane is perpendicular to a length direction of the treatment couch.

9. An apparatus for detecting a position, comprising: a processor and a memory, wherein the memory is configured to store instructions executed by the processor, and the processor is configured to perform the instructions stored in the memory to implement the method for detecting a position according to claim 6.

10. A method for detecting a position, the method comprising:
receiving a deviation sent by an optical tracking system, the deviation being a deviation between a relative position and a reference position, the relative position being a relative position between a mark point set on a treatment body part of a patient and a mark reference point detected by the optical tracking system; and
determining whether to adjust a position of a treatment couch based on the deviation and a deviation range.

11. The method according to claim 10, wherein the determining whether to adjust a position of a treatment couch based on the deviation and a deviation range comprises one of mode (a), mode (b), or mode (c), wherein:
the mode (a) comprises:
detecting whether the deviation is within the deviation range, and
adjusting, when it is detected that the deviation is not within the deviation range, the position of the treatment couch;
the mode (b) comprises:
detecting whether each deviation received in a first duration is within the deviation range, and
adjusting, when it is detected that a number of deviations not within the deviation range is greater than a number threshold, the position of the treatment couch; and
the mode (c) comprises:
instructing, when it is detected that the deviation is not within the deviation range, to turn off a radiation source,
detecting whether consecutively received M deviations are all within the deviation range in a second duration after the radiation source is turned off, M being an integer greater than 1,
keeping, when the consecutively received M deviations are not within the deviation range, the radiation source off and adjusting the position of the treatment couch, otherwise, instructing to turn on the radiation source in the second duration.

12. The method according to claim 11, wherein
the determining whether to adjust a position of a treatment couch based on the deviation and a deviation range comprises:
determining whether to adjust the position of the treatment couch according to the mode (b) or the mode (c) in a first stage of a radiotherapy process from turning on of the radiation source to completing of radiotherapy in the radiotherapy process.

13. The method according to claim 12, wherein
the determining whether to adjust a position of a treatment couch based on the deviation and a deviation range comprises:
determining whether to adjust the position of the treatment couch according to the mode (a) or the mode (b) in a second stage of the radiotherapy process prior to the first stage.

14. The method according to claim 10, wherein before the receiving a deviation sent by an optical tracking system, the method further comprises:
receiving a position offset sent by an image-guided radiotherapy IGRT system and/or the optical tracking system; and
adjusting the position of the treatment couch based on the position offset to complete a position of the patient.

15. The method according to claim 14, wherein before the patient is positioned, the method further comprises:
starting the optical tracking system and the image-guided radiotherapy IGRT system, and loading a treatment plan, the treatment plan comprising N gamma angles at which a treatment to be performed, and N being an integer greater than or equal to 1; and
adjusting a gamma angle to an $n^{th}$ gamma angle according to the treatment plan, the gamma angle being an angle between a plane, where a support panel of a support frame for supporting the patient is located and a vertical plane, the vertical plane being perpendicular to a length direction of the treatment couch, and n being a positive integer less than or equal to N.

16. The method according to claim 15, wherein an initial value of n is 1; when n is less than N after positioning and radiotherapy of the patient is completed at the $n^{th}$ gamma angle, the method further comprises:

adjusting the gamma angle to an n+1$^{th}$ gamma angle, and updating n to n+1 according to the treatment plan.

17. The method according to claim 15, wherein before the gamma angle is adjusted to a first gamma angle according to the treatment plan, the method further comprises:

after positioning of the patient is completed at any one of N gamma angles at which a treatment to be performed, adjusting the gamma angle from the first gamma angle to a N$^{th}$ gamma angle sequentially, and performing a simulated anti-collision detection at each of the N gamma angles.

18. An apparatus for detecting a position, comprising: a processor and a memory, wherein the memory is configured to store instructions executed by the processor, and the processor is configured to perform the instructions stored in the memory to implement the method for detecting a position according to claim 10.

* * * * *